US00PP16554P2

(12) United States Plant Patent
Bergman

(10) Patent No.: US PP16,554 P2
(45) Date of Patent: May 16, 2006

(54) ***CHRYSANTHEMUM* PLANT NAMED 'YONIAGARA FALLS'**

(50) Latin Name: *Chrysanthemum×morifolium*
Varietal Denomination: Yoniagara Falls

(75) Inventor: Wendy R. Bergman, Lehigh Acres, FL (US)

(73) Assignee: Yoder Brothers, Inc., Barberton, OH (US)

( * ) Notice: Subject to any disclaimer, the term of this patent is extended or adjusted under 35 U.S.C. 154(b) by 49 days.

(21) Appl. No.: 11/055,808

(22) Filed: Feb. 11, 2005

(51) Int. Cl.
*A01H 5/00* (2006.01)

(52) U.S. Cl. ..... Plt./286

(58) Field of Classification Search ..... Plt./286
See application file for complete search history.

*Primary Examiner*—Anne Marie Grunberg
*Assistant Examiner*—Annette H Para
(74) *Attorney, Agent, or Firm*—C. A. Whealy

(57) ABSTRACT

A new and distinct cultivar of *Chrysanthemum* plant named 'Yoniagara Falls', characterized by its uniform and somewhat outwardly spreading plant habit; strong and freely branching growth habit; dark green-colored foliage; uniform flowering response and habit; typically grown as a spray-type; early flowering habit; daisy-type inflorescences with elongated oblong-shaped ray florets; white and red purple bi-colored ray florets and green-colored disc florets that develop slowly; and good postproduction longevity with plants maintaining good substance and color for about three to four weeks in an interior environment.

2 Drawing Sheets

Botanical classification/cultivar designation: *Chrysanthemum×morifolium* cultivar Yoniagara Falls.

BACKGROUND OF THE INVENTION

The present Invention relates to a new and distinct cultivar of *Chrysanthemum* plant, botanically known as *Chrysanthemum×morifolium* and hereinafter referred to by the name 'Yoniagara Falls'.

The new *Chrysanthemum* is a product of a planned breeding program conducted by the Inventor in Salinas, Calif. and Fort Myers, Fla. The objective of the program is to create or discover new potted *Chrysanthemum* cultivars that are suitable for year-round production with uniform plant growth habit, good vigor and strong branching habit, numerous inflorescences, desirable inflorescence form and floret colors, fast and uniform flowering response, and good postproduction longevity.

The new *Chrysanthemum* originated from a cross-pollination made by the Inventor in November, 1999, in Salinas, Calif., of a proprietary *Chrysanthemum* seedling selection identified as code number YB-A1403, not patented, as the female, or seed, parent with a proprietary *Chrysanthemum* seedling selection identified as code number YB-A1111, not patented, as the male, or pollen, parent. The new *Chrysanthemum* was discovered and selected by the Inventor in November, 2000, as a single flowering plant from within the resulting progeny of the stated cross-pollination grown in a controlled environment in Fort Myers, Fla.

The selection of this plant was based on its uniform plant growth habit, good vigor and strong branching habit, numerous inflorescences, desirable inflorescence form and floret colors, fast and uniform flowering response, and good postproduction longevity.

Asexual reproduction of the new *Chrysanthemum* by vegetative tip cuttings was first conducted in Fort Myers, Fla. in March, 2001. Asexual reproduction by cuttings has shown that the unique features of this new *Chrysanthemum* are stable and reproduced true to type in successive generations.

SUMMARY OF THE INVENTION

The cultivar Yoniagara Falls has not been observed under all possible environmental conditions. The phenotype may vary somewhat with variations in environment such as temperature, daylength, and/or light level, without, however, any variance in genotype.

The following traits have been repeatedly observed and are determined to be the unique characteristics of 'Yoniagara Falls'. These characteristics in combination distinguish 'Yoniagara Falls' as a new and distinct *Chrysanthemum:*

1. Uniform and somewhat outwardly spreading plant habit.
2. Strong and freely branching growth habit.
3. Dark green-colored foliage.
4. Uniform flowering response and habit.
5. Typically grown as a spray-type.
6. Early flowering, eight week response time.
7. Daisy-type inflorescences with elongated oblong-shaped ray florets.
8. White and red purple bi-colored ray florets and green-colored disc florets that develop slowly.
9. Good postproduction longevity with plants maintaining good substance and color for about three to four weeks in an interior environment.

Plants of the new *Chrysanthemum* can be compared to plants of the female parent selection. Plants of the new *Chrysanthemum* differ from plants of the female parent selection primarily in ray floret coloration as plants of the female parent selection have bronze-colored ray florets.

Plants of the new *Chrysanthemum* can be compared to plants of the male parent selection. Plants of the new *Chrysanthemum* differ from plants of the male parent selection in plant form as plants of the male parent selection are more outwardly spreading than plants of the new *Chrysanthemum*. Plants of the new *Chrysanthemum* and the male parent selection also differ in ray floret coloration as plants of the male parent selection have white and pink bi-colored ray florets. In addition, disc florets of plants of the new *Chrysanthemum* do not produce pollen whereas disc florets of plants of the male parent selection produce pollen.

Plants of the new *Chrysanthemum* can be compared to plants of the cultivar Little Firock, disclosed in U.S. Plant Pat. No. 13,036. In side-by-side comparisons conducted in Fort Myers, Fla., plants of the new *Chrysanthemum* differed from plants of the cultivar Little Firock in the following characteristics:

1. Plants of the new *Chrysanthemum* were shorter than plants of the cultivar Little Firock.
2. Plants of the new *Chrysanthemum* flowered about one week earlier than plants of the cultivar Little Firock.
3. Ray florets of plants of the new *Chrysanthemum* did not twist with development whereas ray florets of plants of the cultivar Little Firock twisted with development.

BRIEF DESCRIPTION OF THE PHOTOGRAPHS

The accompanying colored photographs illustrate the overall appearance of the new *Chrysanthemum* showing the colors as true as it is reasonably possible to obtain in colored reproductions of this type. Colors in the photographs may differ from the color values cited in the detailed botanical description which accurately describe the colors of the new *Chrysanthemum*.

The photograph on the first sheet comprises a side perspective view of typical flowering plants of 'Yoniagara Falls' grown as spray-types.

The photograph on the second sheet comprises a close-up view of typical inflorescences of 'Yoniagara Falls' grown as spray-types.

DETAILED BOTANICAL DESCRIPTION

In the following description, color references are made to The Royal Horticultural Society Colour Chart, 1995 Edition, except where general terms of ordinary dictionary significance are used. The aforementioned photographs, following observations and measurements describe plants grown and flowered during the autumn in Salinas, Calif., in a fiberglass-covered greenhouse and under conditions which approximate those generally used in commercial potted *Chrysanthemum* production. During the production of these plants, the following conditions were measured: day temperatures, 21 to 27° C.; night temperatures, 17 to 19° C.; and light levels, 5,000 to 6,000 foot-candles. Four unrooted cuttings were directly stuck in 15-cm containers, exposed to long day/short night conditions, and pinched once about two weeks later. At the time of the pinch, the photoinductive short day/long night treatments were initiated. Plants used for the description were grown as spray-types. Measurements and numerical values represent averages of typical flowering plants.

Botanical classification: *Chrysanthemum×morifolium* cultivar Yoniagara Falls.

Commercial classification: Daisy-type potted *Chrysanthemum*.

Parentage:

*Female, or seed, parent.*—Proprietary *Chrysanthemum×morifolium* seedling selection identified as code number YB-A1403, not patented.

*Male, or pollen, parent.*—Proprietary *Chrysanthemum×morifolium* seedling selection identified as code number YB-A1111, not patented.

Propagation:

*Type.*—Terminal tip cuttings.

*Time to initiate roots.*—About four days at 21° C.

*Time to produce a rooted cutting.*—About ten days at 21° C.

*Root description.*—White, close to 155D; fibrous.

*Rooting habit.*—Freely branching; moderately dense.

Plant description:

*Appearance.*—Herbaceous daisy-type potted *Chrysanthemum* that is typically grown as a spray-type. Upright with lateral branches somewhat outwardly spreading; uniformly mounded crown. Strong and freely branching growth habit; about three to four lateral branches develop after removal of terminal apex (pinching); dense and full plants.

*Plant height.*—About 28 cm.

*Plant width.*—About 35 cm.

*Lateral branches.*—Length: About 22 cm. Diameter: About 4 mm. Internode length: About 2.1 cm. Strength: Strong. Texture: Pubescent. Color: Darker green than 144A.

*Foliage description.*—Arrangement: Alternate; simple. Length: About 7 cm. Width: About 5.3 cm. Apex: Mucronate. Base: Attenuate with truncate tendencies. Margin: Palmately lobed, sinuses between lateral lobes parallel to convergent. Texture, upper and lower surfaces: Pubsecent. Color: Developing foliage, upper surface: Darker green than 147A. Developing foliage, lower surface: Close to 147B. Fully expanded foliage, upper surface: More green than 147A. Fully expanded foliage, lower surface: Close to 147B. Venation, upper surface: Close to 147A to 147B. Venation, lower surface: Close to 147B. Petiole length: About 2.2 cm. Petiole diameter: About 2.5 mm. Petiole color, upper surface: Close to 147A to 147B. Petiole color, lower surface: Close to 147B.

Inflorescence description:

*Appearance.*—Daisy-type inflorescence form with elongated oblong-shaped ray florets. Inflorescences borne on terminals above foliage. Disk and ray florets develop acropetally on a capitulum. Inflorescences not fragrant.

*Flowering response.*—Under natural conditions, plants flower in the autumn/winter in the Northern Hemisphere. At other times of the year, inflorescence initiation and development can be induced under short day/long night conditions (at least 13.5 hours of darkness). Early flowering; plants exposed to two weeks of long day/short night conditions followed by photoinductive short day/long night conditions flower about eight weeks later.

*Postproduction longevity.*—Inflorescences maintain good color and substance for about three to four weeks in an interior environment.

*Quantity of inflorescences.*—Grown as a spray-type, about ten inflorescences develop per lateral branch.

*Inflorescence bud.*—Height: About 7 mm. Diameter: About 9 mm. Shape: Oblate. Color: Close to 146A.

*Inflorescence diameter.*—About 5.1 cm.

*Inflorescence depth* (*height*).—About 1 cm.

*Diameter of disc.*—About 1.4 cm.

*Receptacle diameter.*—About 6 mm.

*Ray florets.*—Shape: Elongated oblong. Orientation: Initially upright, eventually perpendicular to the peduncle. Aspect: Mostly straight. Length: About 2.5 cm. Width: About 1 cm. Corolla tube length: About 3.5 mm. Corolla tube diameter: About 2 mm. Apex: Acute or emarginate. Base: Fused into a corolla tube. Margin: Entire. Texture, upper and lower surfaces: Smooth, glabrous; satiny. Number of ray florets per inflorescence: About 20 arranged in about two whorls. Color: When opening and fully opened, upper surface: Towards the apex, close to 155D; towards the base, 155D overlain with close to 71A. When opening and fully opened, lower surface: Towards the apex, close to 155D; towards the base, close to 155D underlain with close to 79A.

*Disc florets.*—Arrangement: Massed at center of receptacle. Shape: Tubular. Apex: Five-pointed. Length: About 6 mm. Diameter, apex: About 2 mm. Diameter, base: About 1 mm. Number of disc florets per inflorescence: Numerous, about 145. Color: Immature: Close to 144A; disc florets develop slowly. Mature, apex: 9A. Mature, mid-section: Close to 145C. Mature, base: Close to 155D.

*Phyllaries.*—Quantity per inflorescence: About 22. Length: About 7 mm. Width: About 2.5 mm. Shape: Lanceolate. Apex: Acute. Base: Truncate. Margin: Entire. Texture, upper surface: Waxy, smooth. Texture, lower surface: Pubescent. Color, upper surface: Close to 144A. Color, lower surface: Close to 146A.

*Peduncles.*—Length, terminal peduncle: About 3.5 cm. Length, fourth peduncle: About 5 cm. Diameter: About 2 mm. Strength: Strong. Texture: Pubescent. Color: Close to 144A to 146A.

*Reproductive organs.*—Androecium: Present on disc florets only. Anther color: Close to 12A. Pollen amount: None observed. Gynoecium: Present on both ray and disc florets. Style color: Close to 144B to 144C. Stigma color: Close to 9A.

*Seed/fruit.*—Seed and fruit production has not been observed.

Disease/pest resistance: Resistance to pathogens and pests common to *Chrysanthemums* has not been observed on plants grown under commercial greenhouse conditions.

It is claimed:

1. A new and distinct cultivar of *Chrysanthemum* plant named 'Yoniagara Falls', as illustrated and described.

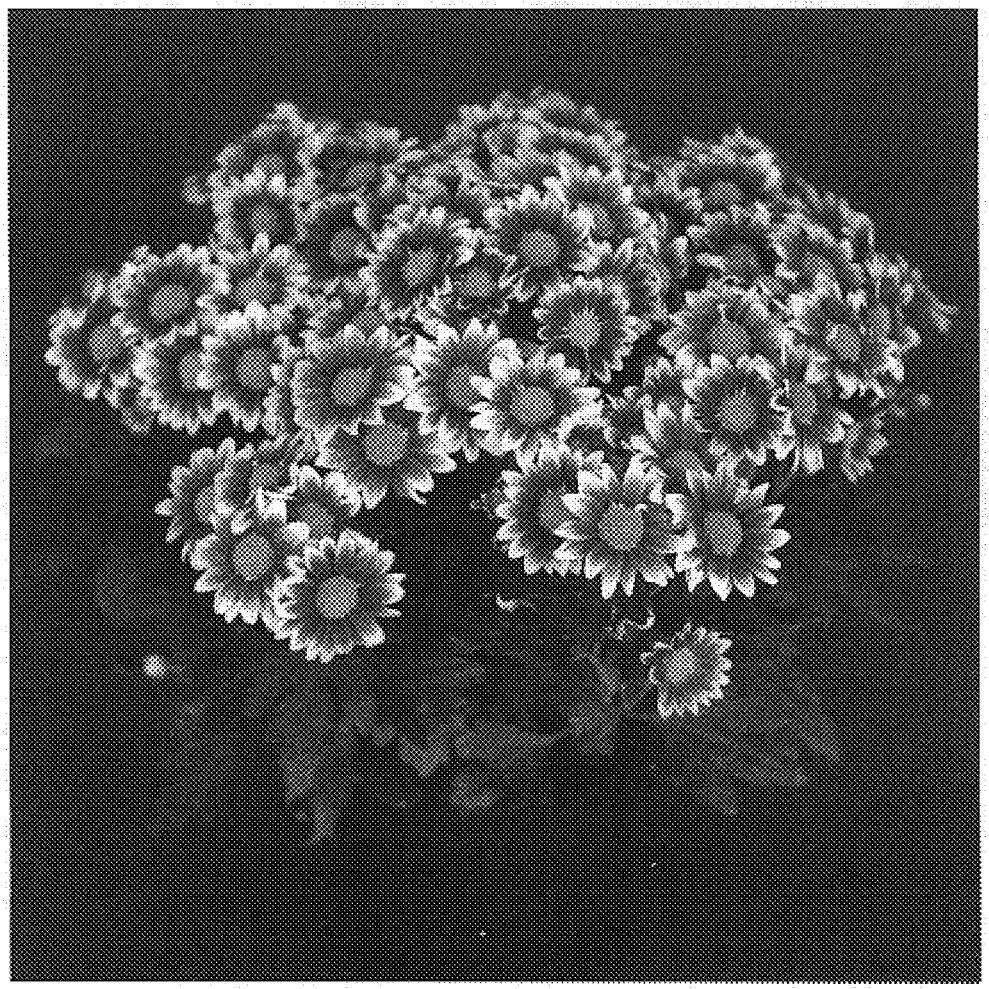

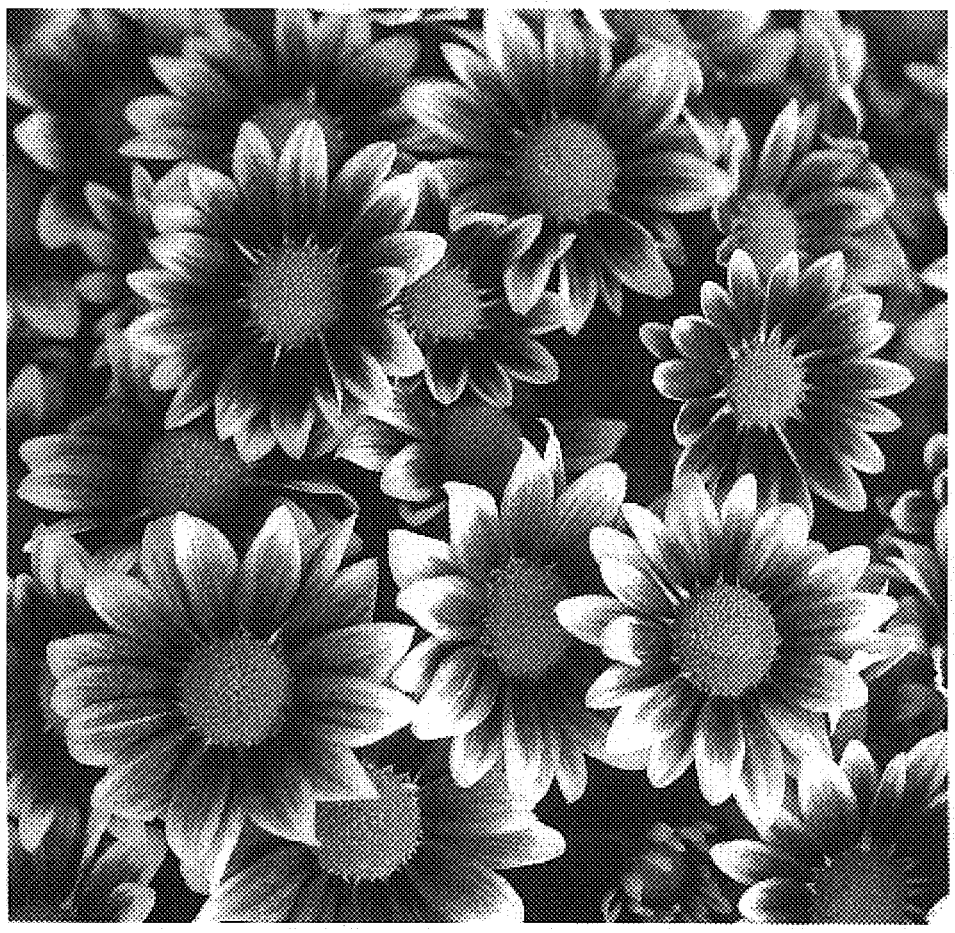

* * * * *